United States Patent
Yang et al.

[11] Patent Number: 5,935,168
[45] Date of Patent: Aug. 10, 1999

[54] GLUTARALDEHYDE-FIXED BIOPROSTHESES

[75] Inventors: Jun Yang, Dove Canyon; Shih-Hwa Shen, Irvine, both of Calif.

[73] Assignee: Baxter International Inc., Deerfield, Ill.

[21] Appl. No.: 09/044,667

[22] Filed: Mar. 20, 1998

Related U.S. Application Data

[62] Division of application No. 08/688,352, Jul. 30, 1996, Pat. No. 5,782,931.

[51] Int. Cl.$^6$ .................................................... A61F 2/02
[52] U.S. Cl. ................................ 623/11; 623/1; 623/2; 8/94.11
[58] Field of Search ........................... 623/11, 1, 2, 12, 623/13, 14, 15; 8/94.11

[56] References Cited

U.S. PATENT DOCUMENTS

| | | |
|---|---|---|
| 3,954,583 | 5/1976 | Lednicer et al. . |
| 3,975,371 | 8/1976 | Lednicer et al. . |
| 4,008,208 | 2/1977 | Lednicer et al. . |
| 4,120,649 | 10/1978 | Schechter . |
| 4,134,867 | 1/1979 | Topfl . |
| 4,245,358 | 1/1981 | Moasser . |
| 4,323,358 | 4/1982 | Lentz et al. . |
| 4,378,224 | 3/1983 | Nimni et al. . |
| 4,396,716 | 8/1983 | Marconi et al. . |
| 4,402,697 | 9/1983 | Pollock et al. . |
| 4,405,327 | 9/1983 | Pollock . |
| 4,549,545 | 10/1985 | Levy . |
| 4,553,974 | 11/1985 | Dewanjee . |

(List continued on next page.)

FOREIGN PATENT DOCUMENTS

| | | |
|---|---|---|
| 0193987 | 9/1986 | European Pat. Off. . |
| 0212933 | 3/1987 | European Pat. Off. . |
| 0411124 | 2/1991 | European Pat. Off. . |
| 2559666 | 2/1984 | France . |
| 745518 | 7/1980 | U.S.S.R. . |
| 1651890 | 5/1991 | U.S.S.R. . |
| 2072206 | 9/1981 | United Kingdom . |
| 2206495 | 1/1989 | United Kingdom . |
| WO 84/01879 | 5/1984 | WIPO . |
| WO 93/19209 | 9/1993 | WIPO . |
| WO 96/04028 | 2/1996 | WIPO . |

OTHER PUBLICATIONS

Bernacca, G. M. et al—Heart Valve, Dis., vol. 1, No. 1, Sep./1992, "In Vitro Calcificatiion of Bioprosthetic Heart Valves: Report of a Novel Method and Review of the Biochemical Factors Involved," pp. 115–130.

Bernacca, G.M. et al, Biomaterials 1992, vol. 13, No. 6—"Chemical modificatiion of bovine pericardium and its effect on calcification in the rat subdermal model."

(List continued on next page.)

*Primary Examiner*—Mickey Yu
*Assistant Examiner*—Dinh X. Nguyen
*Attorney, Agent, or Firm*—Guy L. Cumberbatch; Robert D. Buyan

[57] ABSTRACT

Methods for treating glutaraldehyde-fixed collagenous tissues to mitigate there propensity for subsequent calcification and to improve durability. Collagenous tissues which have been harvested and cross-linked by glutaraldehyde are exposed to a carboxyl activating agent to convert the free carboxyl (COOH) groups of the collagen molecules to activated carboxyl moieties (e.g., o-acylisourea). Thereafter, the collagenous tissue is exposed to a compound capable of reacting with the activated carboxyl moieties (e.g., o-acylisourea) to form non-carboxyl side groups. Monofunctional and multifunctional amines are examples of compounds which may be utilized to react with the activated carboxyl moieties to form such non-carboxyl side groups. Thereafter, the collagenous tissue is again exposed to glutaraldehyde. If the non-carboxyl side groups have functional amino groups ($NH_2$), such additional exposure to glutaraldehyde will result in additional glutaraldehyde cross-linking of the collagen molecules and resultant improvement of durability.

19 Claims, 4 Drawing Sheets

U.S. PATENT DOCUMENTS

| | | |
|---|---|---|
| 4,648,881 | 3/1987 | Carpentier et al. . |
| 4,753,652 | 6/1988 | Langer et al. . |
| 4,759,758 | 7/1988 | Gabbay . |
| 4,772,288 | 9/1988 | Borner et al. . |
| 4,830,847 | 5/1989 | Benedict et al. . |
| 4,831,065 | 5/1989 | Pietsch et al. . |
| 4,838,888 | 6/1989 | Nashef . |
| 4,885,005 | 12/1989 | Nashef et al. . |
| 4,958,008 | 9/1990 | Petite et al. . |
| 4,976,733 | 12/1990 | Girardot . |
| 4,994,237 | 2/1991 | Login et al. . |
| 4,996,054 | 2/1991 | Pietsch et al. . |
| 5,002,566 | 3/1991 | Carpentier et al. . |
| 5,011,913 | 4/1991 | Benedict et al. . |
| 5,051,401 | 9/1991 | Sikes . |
| 5,080,670 | 1/1992 | Imamura et al. . |
| 5,094,661 | 3/1992 | Levy et al. . |
| 5,104,405 | 4/1992 | Nimni . |
| 5,147,514 | 9/1992 | Mechanic . |
| 5,165,919 | 11/1992 | Sasaki et al. . |
| 5,296,583 | 3/1994 | Levy . |
| 5,314,874 | 5/1994 | Miyata et al. . |
| 5,326,370 | 7/1994 | Love et al. . |
| 5,332,475 | 7/1994 | Mechanic . |
| 5,336,616 | 8/1994 | Livesey et al. . |
| 5,368,608 | 11/1994 | Levy et al. . |
| 5,423,887 | 6/1995 | Love et al. . |
| 5,436,291 | 7/1995 | Levy et al. . |
| 5,437,287 | 8/1995 | Phillips et al. . |
| 5,447,536 | 9/1995 | Girardot et al. . |
| 5,476,516 | 12/1995 | Seifter et al. . |

OTHER PUBLICATIONS

Tingfei Xi et al, Journal of Biomedical Materials Research, vol. 26, pp. 1241–1251 (1992) "Prevention of tissue calcification on bioprosthetic heart valve by using epoxy compounds: A study of calcificatiion tests in vitro and in vivo."

Yi Dinghua, et al., Proceedings of Chinese Tissue Valve Conference, Beijing, China 1995, "Study of Calcification Mechanism and Anticalcification on Cardiac Bioprostheses," pp. 17–22 (Abstract).

GLUTARALDEHYDE-FIXED BIOPROSTHESES

This application is a division of application Ser. No. 08/688,352 filed Jul. 30, 1996 now U.S. Pat. No. 5,782,931.

FIELD OF THE INVENTION

The present invention relates generally to methods of manufacturing bioprosthetic devices, and more particularly to a method for mitigating calcification and improving durability of glutaraldehyde-fixed bioprosthetic devices.

BACKGROUND OF THE INVENTION

The prior art has included numerous methods for chemically "fixing" (i.e., tanning) biological tissues. Such chemical fixing of the biological tissues is often used as a means of preserving such tissues so that they may be used as, or incorporated into, bioprosthetic devices which are implanted in or attached to a patient's body. Examples of fixed biological tissues which have heretofore been utilized as bioprostheses include cardiac valves, blood vessels, skin, dura mater, pericardium, ligaments and tendons. These tissues typically contain connective tissue matrices which act as the supportive framework of the tissues. The cellular parenchyma of each tissue is disposed within and supported by it's connective tissue matrix.

Collagen and elastin are two substances which make up the connective tissue framework of most biological tissues. The pliability or rigidity of each biological tissue is largely determined by the relative amounts of collagen and elastin present within the tissue and/or by the physical structure and confirmation of the connective tissue frame work.

Each Collagen molecule consists of three (3) polypeptide chains which are intertwined in a coiled helical confirmation. Chemical fixatives (i.e., tanning agents) used to preserve collagenous biological tissues generally form chemical cross-linkages between the amino groups on the polypeptide chains within a given collagen molecules, or between adjacent collagen molecules.

The chemical cross-linkages formed between polypeptide chains within a single collagen molecule are termed "intramolecular", while the cross-linkages formed between polypeptide chains of different collagen molecules are termed "intermolecular".

Chemical fixative agents which have been utilized to cross-link collagenous biological tissues include; formaldehyde, glutaraldehyde, dialdehyde starch, hexamethylene diisocyanate and certain polyepoxy compounds.

In particular, glutaraldehyde has proven to be a suitable agent for fixing various biological tissues used for subsequent surgical implantation. Indeed, glutaraldehyde has become widely used as a chemical fixative for many commercially available bioprostheses, such as; porcine bioprosthetic heart valves (i.e., the Carpentier-Edwardss stented porcine bioprosthesis; Baxter Healthcare Corporation; Edwards CVS Division, Irvine, Calif. 92714-5686), bovine pericardial heart valve prostheses (e.g., Carpentier-Edwards SPericardial Bioprosthesis, Baxter Healthcare Corporation, Edwards CVS Division; Irvine, Calif. 92714-5686) and stentless porcine aortic prostheses (e.g., Edwardss PRIMAM Stentless Aortic Bioprosthesis, Baxter Edwards AG, Spierstrasse 5, GH6048, Horn, Switzerland).

One problem associated with the implantation of bioprosthetic materials is that collagen and elastin typically contained in these materials tend to undergo calcification. Such calcification can result in undesirable stiffening or degradation of the bioprosthesis. Both intrinsic and extrinsic calcification are known to occur in fixed collagenous bioprostheses, although the exact mechanism(s) by which such calcification occurs is unknown.

Clinical experience and experimental data has taught that glutaraldehyde-fixed collagenous bioprostheses may tend to calcify sooner than bioprostheses which have been fixed by other nonaldehyde fixative agents. Such accelerated calcification of glutaraldehyde-fixed bioprostheses has been reported to occur most predominantly in pediatric patients. (Carpentier et al., Continuing Improvements in Valvular Bioprostheses, J. Thorac Cardiovasc. Surg. 83:27–42, 1982.) Such accelerated calcification is undesirable in that it may lead to deterioration and/or failure of the implanted bioprostheses. In view of this propensity for accelerated calcification of glutaraldehyde-fixed bioprostheses in young patients, surgeons typically opt to implant mechanical heart valves or homografts (if available) into pediatric or relatively young patients (i.e., patients under 65 years of age), rather than glutaraldehyde-fixed bioprosthetic valves. However, patients who receive mechanical valve implants require ongoing treatment with anticoagulant medications, which can be associated with increased risk of hemorrhage. Also, homografts are of limited availability and may carry pathogens which can result in infection.

The factors which determine the rate at which glutaraldehyde-fixed bioprosthetic grafts undergo calcification have not been fully elucidated. However, factors which are thought to influence the rate of calcification include:

a) patient's age;
b) existing metabolic disorders (i.e., hypercalcemia, diabetes, etc.);
c) dietary factors;
d) race;
e) infection;
f) parenteral calcium administration;
g) dehydration;
h) distortion/mechanical factors;
i) inadequate coagulation therapy during initial period following surgical implantation; and
j) host tissue responses.

Many investigators have attempted to discover ways of mitigating the in situ calcification of glutaraldehyde-fixed bioprostheses. Included among these calcification mitigating techniques are the methods described in U.S. Pat. No. 4,885,005 (Nashef et al.) entitled Surfactant Treatment of Implantable Biological Tissue To Inhibit Calcification; U.S. Pat. No. 4,648,881 (Carpentier et al.) entitled Implantable Biological Tissue and Process For Preparation Thereof; U.S. Pat. No. 4,976,733 (Girardot) entitled Prevention of Prosthesis Calcification; U.S. Pat, No. 4,120,649 (Schechter) entitled Transplants; U.S. Pat. No. 5,002,2566 (Carpentier) entitled Calcification Mitigation of Bioprosthetic Implants; EP 103947A2 (Pollock et al.) entitled Method For Inhibiting Mineralization of Natural Tissue During Implantation and WO 84/01879 (Nashef et al.) entitled Surfactant Treatment of Implantable Biological Tissue to Inhibit Calcification; and, in Yi, D., Liu, W., Yang, J., Wang, B., Dong, G., and Tan, H.; *Study of Calcification Mechanism and Anticalcification On Cardiac Bioprostheses* Pgs. 17–22, Proceedings of Chinese Tissue Valve Conference, Beijing, China, June 1995.

There remains a need in the art for the development of new methods for inhibiting or mitigating calcification of glutaraldehyde-fixed biological tissues.

SUMMARY OF THE INVENTION

The present invention provides methods for treating glutaraldehyde cross-linked tissues which contain collagen and/or elastin so as to mitigate the propensity for subsequent calcification of such tissues, by replacing at least some of the carboxyl groups present on the collagen and/or elastin molecules with non-carboxyl side groups to thereby eliminate the sites whereby calcium may become chemically or physically attached to the protein (i.e., collagen, elastin) molecules. Thereafter, the bioprosthesis may be again immersed in or exposed to glutaraldehyde. If the non-carboxyl side groups formed on the collagen and/or elastin molecules include glutaraldehyde-reactive groups. (e.g., $NH_2$ groups), the subsequent exposure to glutaraldehyde will result in the formation of additional glutaraldehyde cross-linkages between said glutaraldehyde-reacting groups.

In accordance with the present invention, there is provided a method which generally comprises the steps of:

a) providing a collagenous bioprosthesis which has been cross-linked with glutaraldehyde;

b) reacting at least some of the carboxyl groups present on collagen molecules of the bioprosthesis with a carboxyl activating agent to convert at least some of the carboxyl groups into activated carboxyl moieties;

c) reacting a carboxyl-free compound with said activated carboxyl moieties, thereby forming carboxyl-free side groups on the collagen molecules of the bioprosthesis.

Additionally, this method may further comprise the additional step of:

d) contacting the bioprosthesis with glutaraldehyde.

The activated carboxyl moieties formed in step d of the above-recited method will typically be o-acylisourea groups of molecular formula CO—.

The bioprosthesis provided in step a of the method may comprise any type of collagenous tissue such as, heart valves, segments of blood vessel, segments of aortic root having an aortic valve positioned therewithin, pericardium, ligaments, tendons, skin, etc. These collagenous tissues may be harvested from any suitable source, and in many instances may be porcine or bovine in origin.

The carboxyl activating agent utilized in step b of the above-summarized method causes the carboxyl (COOH) groups which are present on the collagen molecules to be converted to activated carboxyl moieties (e.g., o-acylisourea), which will react with amino groups. Examples of carboxyl activator compounds which may be utilized for this purpose include the following: 1-ethyl-3-(3-dimethylaminopropyl)-carbodiimide hydrochloride (EDC); dihexylcarbodiimide (DCC); 1-ethyl-3-(4-azonia-4,4-dimethylpentyl)carbodiimide iodide (EAC). In many applications 1-ethyl-3-(3-dimethylaminopropyl)-carbodiimide hydrochloride (EDC) is the preferred carboxyl-activating agent.

In step c of the method, a non-carboxyl compound, such as an amine, is reacted with the activated carboxyl moieties (e.g., o-acylisourea) formed in step b, to form non-carboxyl side groups on the collagen molecules, in place of the previously existing carboxyl (COOH) groups. Due to the relation instability of the activated carboxyl moiety (e.g., o-acylisourea), it is typically desirable to perform step c (reaction with non-carboxyl compound) immediately after completion of step b (formation of the activated carboxyl moieties (e.g., o-acylisourea)). Thus, the carboxy-activating agent used in step b and the non-carboxyl reactant compound used in step c may desirably be combined in a single solution in which the collagenous tissue may be immersed.

The non-carboxyl side groups formed in step c of the method have less propensity for calcification than did the previously-present carboxyl (COOH) side groups of the collagen molecules. Amines are one type of non-carboxyl compound which may be reacted with the activated carboxyl moieties (e.g., o-acylisourea), to form the desired non-carboxyl side groups on the collagen molecules. When an amine compound is used for this purpose, the non-carboxyl side groups formed thereby will be bound to the activated carboxyl moieties (e.g., o-acylisourea) by way of amide linkages therewith. Either monofunctional or multifunctional amines may be used for this purpose. When monofunctional amines are used for this purpose, the only functional amino group will be utilized in forming the amide band and the resultant non-carboxyl side groups formed thereby will be free of any remaining amine functionalities. On the other hand, if multifunctional amine compounds are used for this purpose, only one functional amino group will be used, in most instances, in forming the amide bond and the resultant non-carboxyl side groups will contain one or more remaining functional amino groups.

In optional step d of the method, the bioprosthesis may again be immersed in or otherwise contacted with glutaraldehyde. If the non-carboxyl side groups formed on the collagen molecules are free of functional amino groups, this additional exposure to glutaraldehyde will not result in further cross-linking of the collagen molecules due to the absence of functional amine bonding sites with which the glutaraldehyde may react. However, if the non-carboxyl side groups formed on the collagen molecules do contain functional amino groups, this further exposure to glutaraldehyde will result in the formation of additional glutaraldehyde cross-linkages between such remaining free amino groups.

The method of the present invention will also serve to replace the carboxyl (COOH) groups of the elastin molecules present in the bioprosthesis, with the same non-carboxyl side groups as described hereabove with respect to the collagen molecules. It will be appreciated that, although the invention is described herein as being directed to collagen molecules in collagenous bioprostheses, most such will also contain varying amounts of elastin, and the chemical effects of the present invention described herein as affecting the collagen molecules will also affect the elastin molecules, due to similarities in the chemical structure of elastin to that of collagen.

Further objects and advantages of the above-summarized invention will become apparent to those skilled in the art upon reading of the detailed description of preferred embodiment set forth herebelow.

DETAILED DESCRIPTION OF THE PREFERRED EMBODIMENT

The following detailed description and the accompanying drawings are provided for purposes of describing and illustrating certain presently preferred embodiments of the invention only, and are not intended to limit the scope of the invention in any way.

Figure 1:
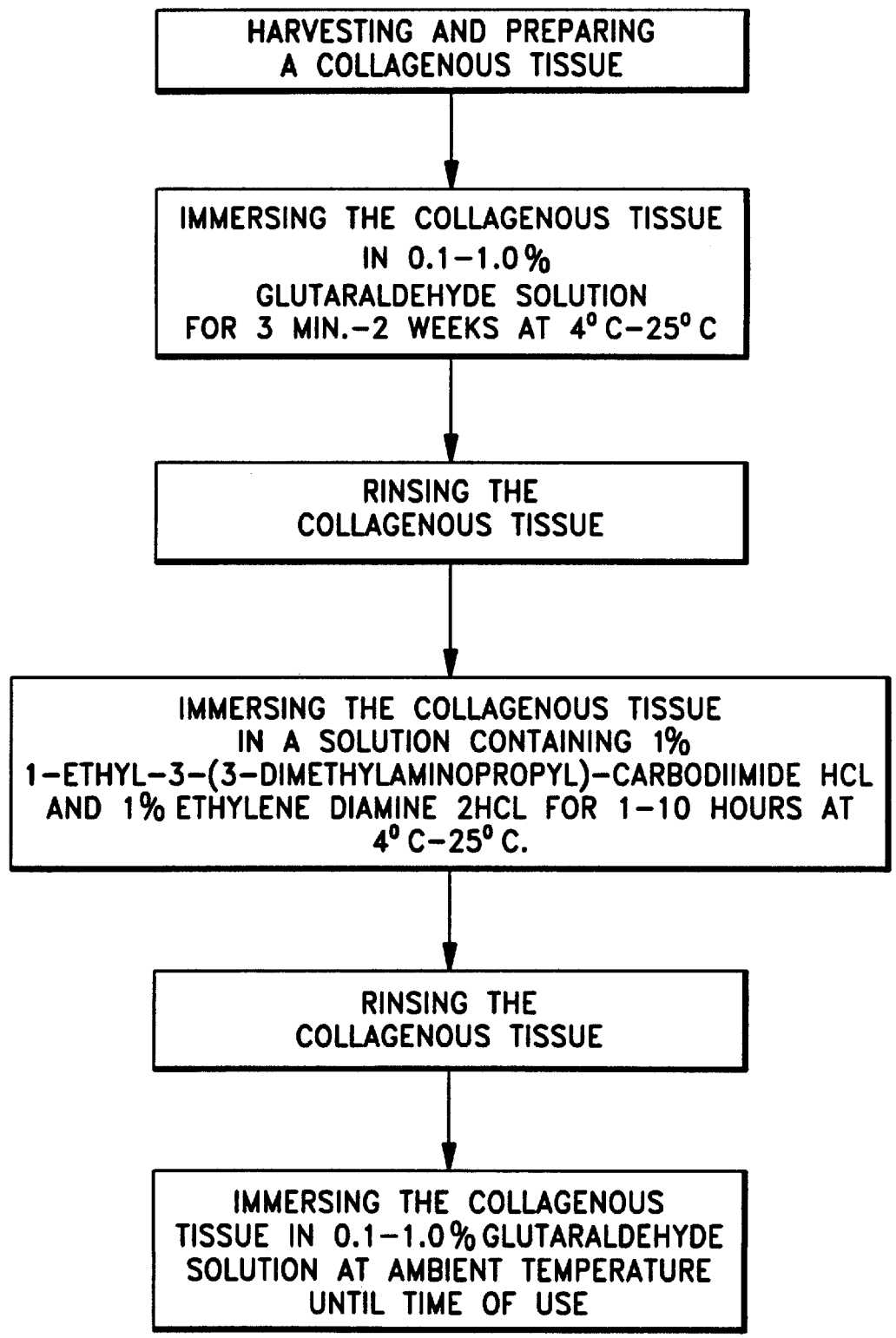
FIG. 1 is a flow diagram of a first preferred embodiment of the method of the present invention.
Figure 2:
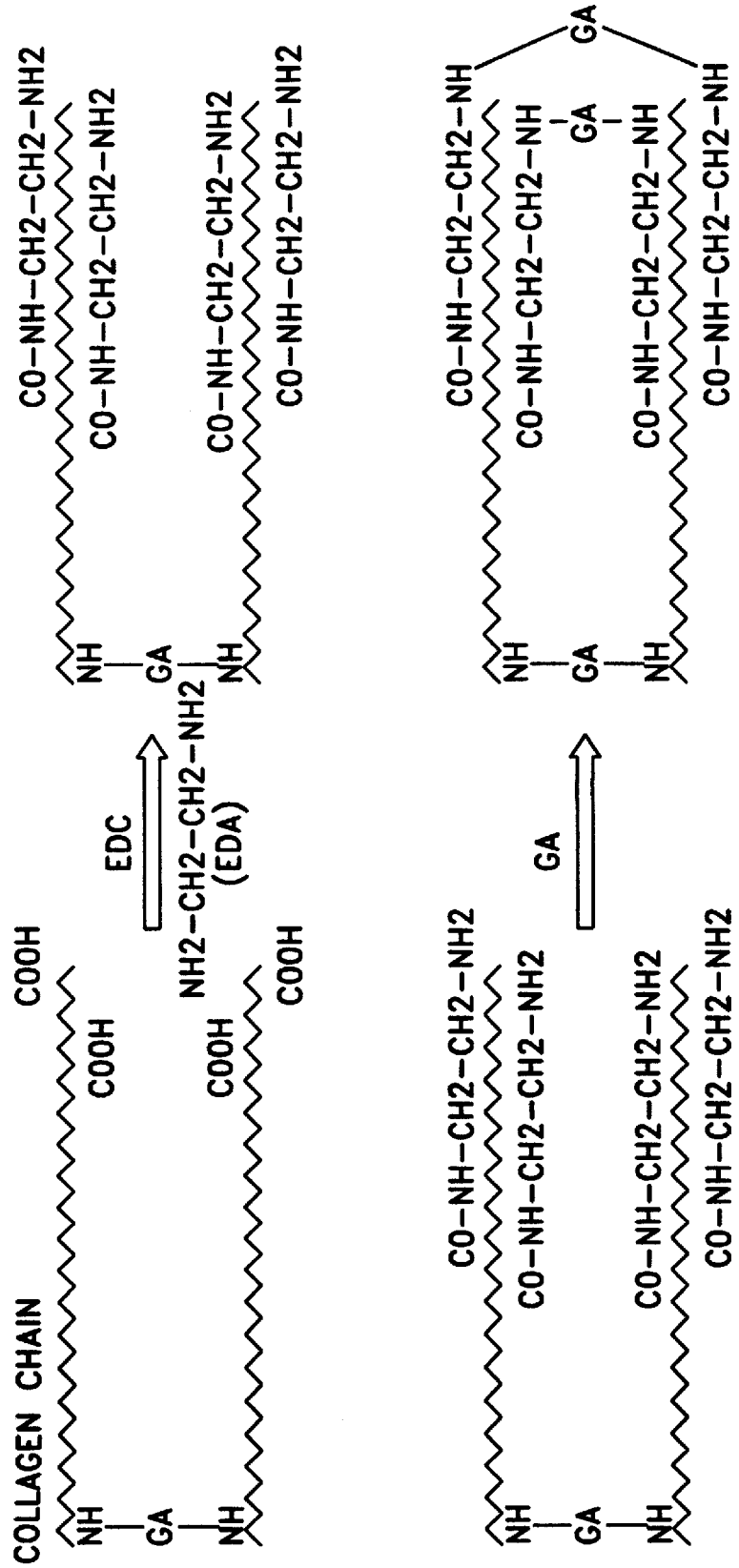
FIG. 2 is a schematic diagram of the chemical reactions which occur in the first preferred embodiment of the method of the present invention shown in the flow diagram of FIG. 1.
Figure 3:
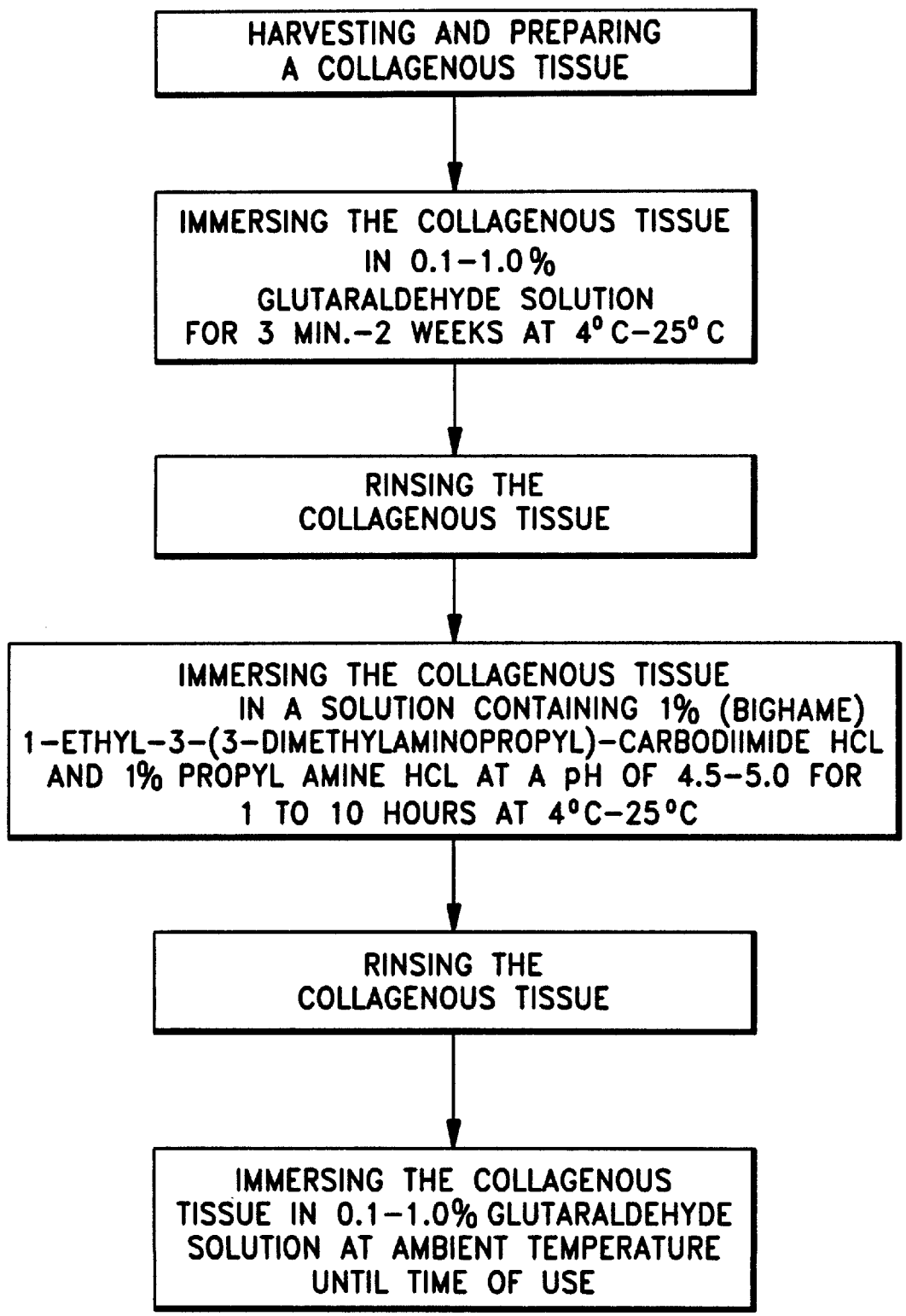
FIG. 3 is a flow diagram of a second preferred embodiment of the method of the present invention.
Figure 4:
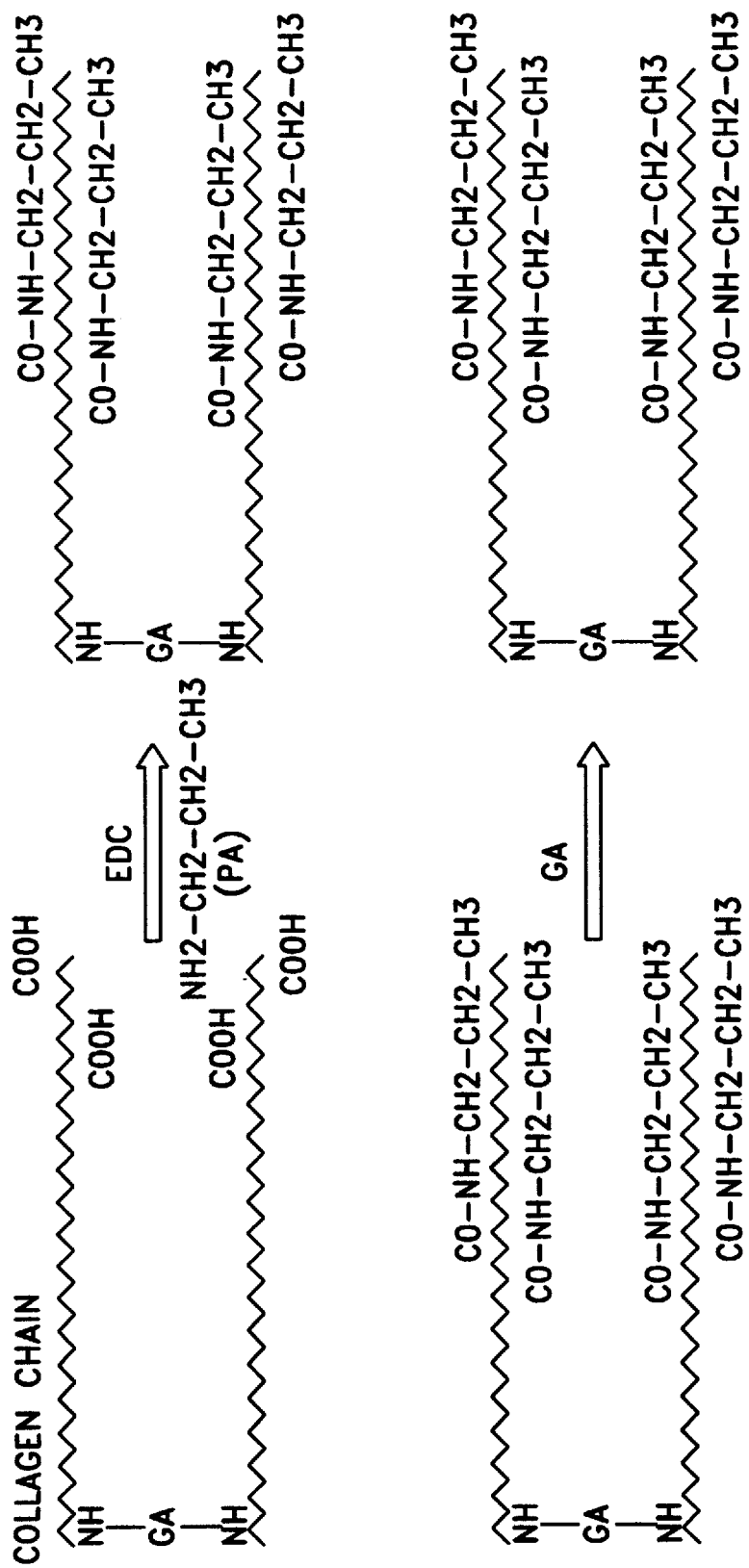
FIG. 4 is a schematic diagram showing the chemical reactions which occur in the second preferred embodiment of the method of the present invention shown in the flow diagram of FIG. 3.

Two (2) embodiments of the invention are shown in the accompanying FIGS. 1–4, and described in detail herebelow. Specifically, FIGS. 1–2 are directed to a first preferred embodiment, while FIGS. 3–4 are directed to a second preferred embodiment.

i. First Preferred Embodiment

Referring to the showings of FIGS. 1–2, the first preferred embodiment of the present invention provides a method for glutaraldehyde cross-linking of a collagenous bioprosthesis (Steps 1–2) followed by subsequent treatment to mitigate it's propensity for subsequent calcification, and to increase it's durability. In this first embodiment of the invention, the naturally occurring carboxyl groups of the collagen molecules are replaced (in Steps 4–5 of the method) by non-carboxyl amide-bound side groups having functional amino groups at the terminal ends thereof. Thereafter, subsequent exposure to glutaraldehyde (Step 6) results in the formation of additional glutaraldehyde cross-linkages between the free amine functionalities of the non-carboxyl side groups. The formation of such additional glutaraldehyde cross linkages results in a modification of the physical properties of the bioprosthesis, and tends to improve the long-term durability thereof.

With reference to the flow diagram of FIG. 1, the method of this first preferred embodiment comprises the following steps:

Step I: Harvesting and Processing a Collagenous Tissue.

A suitable collagenous tissue is harvested from a mammal, and is trimmed, cleaned and prepared in accordance with standard technique.

Step II: Glutaraldehyde Fixation

In the second step of this method, the previously-prepared collagenous tissue is immersed in 0.1–1.0% glutaraldehyde solution for 30 min. to 2 weeks at 4° C.–25° C. to effect glutaraldehyde cross linking between free amino groups located on the collagen molecules of the collagenous tissue.

Step III: Rinsing

After the collagenous tissue is removed from the glutaraldehyde solution, it is rinsed with a suitable phosphate-free rinsing solution, such as 0.9% NaCl solution or HEPES buffer saline. This rinsing removes residual glutaraldehyde solution from the collagenous tissue. It is desirable that the rinsing solution be free of phosphates because the presence of residual phosphates on the collagenous tissue can shorten the half-life or impair the stability of the carbodimide compound(s) used in the following step IV (described herebelow).

Step IV: Carboxyl Activation and Formation of Non-Carboxyl Side Groups Having ANLine Functionality In this fourth step of the method, the previously glutaraldehyde-fixed collagenous tissue is immersed in a solution of 1% 1-ethyl-3-(3-dimethylaminopropyl) carbodiimide HCl (EDC) and 1% ethylene diamine 2 HCl (EDA) at a pH of 4.5 to 5.0, to a) convert the carboxyl (COOH) groups of the collagen molecules to activated carboxyl moieties (e.g., o-acylisourea), and b) to form amide-bound, non-carboxyl side groups on the collagen molecules. The non-carboxyl side groups contain free functional amino groups on the terminal ends thereof.

Step V: Rinsing

After the collagenous tissue is removed from the EDC/EDA solution, it is rinsed with a suitable rinsing solution, such as phosphate buffered saline. This rinsing removes residual EDC and EDA from the collagenous tissue.

Step VI: Further Glutaraldehyde Treatment

In this sixth step of the method, the collagenous tissue is immersed in 0.1–1.0% glutaraldehyde solution at ambient temperature, until the time of surgical implantation of the bioprosthesis or subsequent manufacturing steps (e.g., cutting and mounting on stents or other framework). This final immersion in glutaraldehyde solution serves to maintain the sterility of the graft until time of use or further manufacturing steps. Furthermore, this final glutaraldehyde treatment results in the creation of additional glutaraldehyde cross-linkages between the collagen molecules, as explained more fully herebelow and as shown in detail in FIG. 2.

FIG. 2 provides a schematic showing of the specific chemical reactions which take place in Steps IV and VI of the above-summarized first embodiment of the method. With reference to FIG. 2, it will be appreciated that the ethylene diamine (EDA) used in Step IV of the method is a straight-chain aliphatic hydrocarbon having terminal amine (NHi) groups located at both ends of the molecule. One of these terminal amine ($NH_2$) groups reacts with the activated carboxyl moiety (e.g., o-acylisourea) to form an amide linkage therewith, while the other terminal amine ($NH_2$) group remains unreacted and available for subsequent cross-linking by glutaraldehyde.

Also as shown in FIG. 2, the final exposure of the collagenous tissue to glutaraldehyde in Step VI of the method results in the formation of additional glutaraldehyde cross-linkages between the free terminal amine ($NH_2$) groups which remain on the non-carboxyl side groups of the collagen molecules.

Thus, the first preferred embodiment of the invention shown in FIGS. 1–2 provides not only for replacement of the carboxyl (COOH) side groups of the collagen molecules with non-carboxyl side groups having mitigated propensity for calcification, but also provides for the formation of additional glutaraldehyde cross-linkages which effect the overall cross-linked density and long-term durability of the bioprosthesis.

ii. Second Embodiment

A second preferred embodiment of the invention is shown in FIGS. 3–4.

In this second preferred embodiment of the invention, a monofunctional amine (propyl amine) is used in Step IV of the method, rather than the difunctional amine (ethylene diamine) of the above-described first embodiment. The single amine ($NH_2$) group on the monofunctional propyl amine molecule reacts with the activated carboxyl moiety (e.g., o-acylisourea) to form an amide linkage therewith. Thus, the resultant carboxyl-free side group contains no remaining functional amine ($NH_2$) groups. In this regard, the replacement of the carboxyl (COOH) groups of the collagen molecules with the carboxyl-free side groups serves to mitigate the propensity of the bioprosthesis for subsequent calcification, but the absence of remaining functional amine ($NH_2$) groups on the carboxyl-free side groups created in Step IV of the method prevents the collagen molecules from undergoing further glutaraldehyde cross-linking during the final exposure to glutaraldehyde.

With reference to the flow diagram of FIG. 3, this second preferred embodiment of the invention is a bioprosthesis preparation method which comprises the steps of:

Step I: Harvesting and Processing a Collagenous Tissue.

A suitable collagenous tissue is harvested from a mammal, and is trimmed, cleaned and prepared in accordance with standard technique.

Step II: Glutaraldehyde Fixation

In the second step of this method, the previously-prepared collagenous tissue is immersed in 0.1–1.0% glutaraldehyde solution for 30 min. to 2 weeks at 4°–25° C. to effect glutaraldehyde cross linking between free amino groups located on the collagen molecules of the collagenous tissue.

Step III: Rinsing

After the collagenous tissue is removed from the glutaraldehyde solution, it is rinsed with a suitable phosphate-free rinsing solution, such as 0.9% NaCl solution or HEPES buffer saline. This rinsing removes residual glutaraldehyde solution from the collagenous tissue. It is desirable that the rinsing solution be free of phosphates because the presence of residual phosphates on the collagenous tissue can shorten the half life or impair the stability of the carbodiimide compound(s) used in the following step IV (described herebelow).

Step IV: Carboxyl Activation and Attachment of non-carboxyl Side Groups

In this fourth step of the method, the collagenous tissue is immersed in a solution of 1% 1-ethyl-3-(3-dimethylaminopropyl)-carbodiimide HCl (EDC) and 1% propyl amine HCl (PA) for a period of 1 to 10 hours at 4° to 25° C./at a pH of 4.5 to 5.0. This results in a) conversion of the carboxyl groups (COOH) present on the collagen molecules to activated carboxyl moieties (e.g., o-acylisourea) and b) amide bonding of the propyl amine (PA) molecules with the activated carboxyl moieties (e.g., o-acylisourea). Thus, the carboxyl groups (COOH) of the collagen chains are replaced by carboxyl-free side groups. These carboxyl-free side groups are devoid of any remaining functional amine (NH$_2$) groups.

Step V: Rinsing

After the collagenous tissue has been removed from the EDC/PA solution, it is rinsed with a suitable rinsing solution such as phosphate buffered saline. This rinsing removes residual EDC and PA from the collagenous tissue.

Step VI: Final Glutaraldehyde Treatment/Sterilization

In this sixth step of the method, the collagenous tissue is immersed in 0.1–1.0% glutaraldehyde solution at ambient temperature until time of surgical implantation of the bioprosthesis or subsequent manufacturing steps (e.g., cutting and mounting on stents or other framework). This results in maintained sterilization of the collagenous tissue until time of use or further manufacturing steps. However, as described more fully herebelow, this additional glutaraldehyde exposure does not result in the formation of additional glutaraldehyde cross-linkages because the non-carboxyl side groups formed on the collagen molecules in Step IV of the method are devoid of functional amino groups which could act as binding sites for the glutaraldehyde.

FIG. 4 is a schematic showing of the chemistry of Steps 4 and 6 of the second embodiment of the method shown in the flow diagram of FIG. 3.

With reference to FIG. 4, the 1-ethyl-3-(3-dimethylaminopropyl)-carbodiimide (EDC) converts the carboxyl (COOH) groups of the collagen chain to activated carboxyl moieties (e.g., o-acylisourea). The single amine (NH$_2$) groups of the propyl amine (PA) molecules then react with the activated carboxyl moieties (e.g., o-acylisourea) to form amide linkages therewith. This results in the formation of non-carboxyl side groups which are devoid of any remaining functional amine (NH$_2$) groups.

As further shown in FIG. 4, the final exposure of the collagenous tissue to glutaraldehyde in Step VI serves to maintain sterility of the collagenous tissue, but does not cause further cross-linking of the collagen molecules due to the absence of functional amine (NH$_2$) sites on the non-carboxyl side groups formed by the propyl amine (PA).

Thus, this second embodiment of the method of the present invention differs from the above-described first embodiment in that no further glutaraldehyde cross-linking occurs during the glutaraldehyde exposure of Step VI. In this regard, the cross-link density of the collagenous tissue remains unaffected by the treatment method of the second embodiment, although the propensity for calcification of the collagenous tissue is significantly decreased due to the replacement of the endogenous carboxyl groups (COOH) with non-carboxyl, amide-bound groups, as shown.

It will be appreciated that the invention has been described hereabove with reference to certain preferred embodiments only. No effort has been made to exhaustively describe all possible embodiments in which the invention may be practiced. It is intended, however that all reasonable modifications, additions, deletions and variations of the above-described preferred embodiments be included within the scope of the following claims.

What is claimed is:

1. A glutaraldehyde-fixed bioprosthesis manufactured by the method comprising the steps of:

a) providing a collagen-containing tissue;

b) contacting said tissue with glutaraldehyde to form a glutaraldehyde cross-linked tissue;

c) rinsing the tissue to remove residual glutaraldehyde such that the tissue is activated carboxyl moieties on the tissue free of exogenous compounds that would deter the subsequent formation of activated carboxyl moieties on the tissue:

d) contacting the glutaraldehyde cross-linked tissue with a carboxyl activator compound capable of converting at least some of the carboxyl groups present on collagen molecules of the tissue to activated carboxyl moieties capable of reacting with amino groups;

e) contacting the tissue with a compound that will react with the activated carboxyl moieties to form noncarboxyl side groups on the collagen molecules; and, thereafter;

f) again contacting said tissue with glutaraldehyde.

2. The bioprosthesis of claim 14 wherein the collagenous tissue provided in step a is selected from the group consisting of:

heart valves;

segments of blood vessel;

segments of aortic root having an aortic valve positioned therewithin;

pericardium;

ligaments;

tendons; and, skin.

3. The bioprosthesis of claim 1 wherein the tissue is of porcine origin.

4. The bioprosthesis of claim 1 wherein the tissue is bovine in origin.

5. The bioprosthesis of claim 1 wherein the compound contacted with the tissue in step e is a carboxyl-free monoamine.

6. The bioprosthesis of claim 5 wherein the carboxyl-free monoamine is aliphatic.

7. The bioprosthesis of claim 6 wherein the carboxyl-free aliphatic monoamine is propyl amine.

8. The bioprosthesis of claim 1 wherein the compound contacted with the tissue in step e is a carboxyl-free diamine.

9. The bioprosthesis of claim 8 wherein the carboxyl-free diamine compound is aliphatic.

10. The bioprosthesis of claim 9 wherein the carboxyl-free, aliphatic diamine compound is ethylene diamine.

11. The bioprosthesis of claim 10, wherein the compound used in step e contains at least two functional amino groups such that at least one functional amino group will remain on each amide-bound side group formed on the collagen molecules in step e, and wherein:

the subsequent contacting of the tissue with glutaraldehyde in step f of the preparation method results in the formation of additional glutaraldehyde cross-linkages between the free amino groups on the amide-bound side groups of the collagen molecules within the tissue.

12. The bioprosthesis of claim 1 wherein the carboxyl activator compound used in step c of the preparation method is a carbodiimide.

13. The bioprosthesis of claim 12 wherein said carbodiimide is selected from the group consisting of:

1-ethyl-3-(3-dimethylaminopropyl)-carbodiimide hydrochloride (EDC);

dihexylcarbodiimide (DCC);

1-ethyl-3-(4-azonia-4,4-dimethylpentyl)carbodiimide iodide (EAC).

14. A glutaraldehyde-fixed collagenous bioprosthesis prepared by a method comprising the steps of:

a) providing a collagenous bioprosthesis which has been cross-linked with glutaraldehyde and is free of exogenous compounds that would deter the subsequent formation of activated carboxyl moieties on the bioprosthesis;

b) reacting at least some of the carboxyl groups present on collagen molecules of the bioprosthesis with a carboxyl activating agent to convert at least some of the carboxyl groups into activated carboxyl moieties; and, c) reacting a carboxyl-free compound with said activated carboxyl moieties, thereby forming carboxyl-free side groups on the collagen molecules of the bioprosthesis.

15. The bioprosthesis of claim 14 wherein the carboxyl activating compound is a carbodiimide.

16. The bioprosthesis of claim 15 wherein the carbodiimide is selected from the group consisting of:

1-ethyl-3-(3-dimethylaminopropyl)-carbodiimide hydrochloride (EDC);

dihexylcarbodiimide (DCC); and, 1-ethyl-3-(4-azonia-4,4-dimethylpentyl)carbodiimide iodide (EAC).

17. The bioprosthesis of claim 14 wherein the carboxyl-free compound is selected from the group consisting of:

amines;

monofunctional amines;

multifunctional amines;

aliphatic monofunctional amines;

aliphatic multifunctional amines;

aliphatic diamines;

propyl amine;

ethylene diamine.

18. The bioprosthesis of claim 14 wherein the method by which the bioprosthesis is prepared further comprises the step of:

d) contacting the bioprosthesis with glutaraldehyde.

19. The bioprosthesis of claim 18 wherein the carboxyl-free compound used in step c is an amine which has at least two functional amino groups such that one functional amino group reacts with the activated carboxyl moiety to form an amide linkage therewith and at least one other functional amino group will remain available for subsequent reaction with glutaraldehyde, and wherein the further exposure to glutaraldehyde in step d results in the formation of additional glutaraldehyde cross-linkages between the functional amino groups which remain in the carboxyl free side groups of the collagen molecules.

* * * * *